(12) United States Patent
Pinchuk et al.

(10) Patent No.: US 6,348,066 B1
(45) Date of Patent: Feb. 19, 2002

(54) MODULAR ENDOLUMINAL STENT-GRAFTS AND METHODS FOR THEIR USE

(75) Inventors: Leonard Pinchuk, Miami, FL (US); Jean-Pierre Dereume, Brussels (BE)

(73) Assignee: Corvita Corporation, Miami, FL (US)

( * ) Notice: Subject to any disclaimer, the term of this patent is extended or adjusted under 35 U.S.C. 154(b) by 0 days.

(21) Appl. No.: 09/134,887

(22) Filed: Aug. 14, 1998

Related U.S. Application Data

(63) Continuation of application No. 08/806,739, filed on Feb. 27, 1997, now abandoned, which is a continuation-in-part of application No. 08/554,694, filed on Nov. 7, 1995, now Pat. No. 5,628,788.

(51) Int. Cl.$^7$ .................................................. A61F 2/06
(52) U.S. Cl. ..................................... 623/1.16; 606/198
(58) Field of Search ............................ 623/1, 12, 1.15, 623/1.16, 1.21; 606/191, 194, 198

(56) References Cited

U.S. PATENT DOCUMENTS

| | | | | |
|---|---|---|---|---|
| 3,105,492 A | * | 10/1963 | Jeckel .......................... | 128/334 |
| 3,304,557 A | * | 2/1967 | Polansky ........................ | 623/1 |
| 3,463,158 A | * | 8/1969 | Schmitt et al. .............. | 128/334 |
| 3,479,670 A | * | 11/1969 | Medell ........................... | 623/1 |
| 3,485,234 A | * | 12/1969 | Stevens ........................ | 128/2 |
| 4,086,665 A | | 5/1978 | Poirier | |
| 4,743,251 A | * | 5/1988 | Barra ............................ | 623/1 |
| 5,064,435 A | * | 11/1991 | Porter ........................... | 623/12 |
| 5,383,892 A | * | 1/1995 | Cardon et al. ............... | 606/198 |
| 5,383,926 A | * | 1/1995 | Lock et al. ..................... | 623/1 |
| 5,405,378 A | * | 4/1995 | Strecker ........................ | 623/1 |
| 5,575,817 A | * | 11/1996 | Martin ........................... | 623/1 |
| 5,609,627 A | * | 3/1997 | Goicoechea et al. .......... | 623/11 |
| 5,628,788 A | * | 5/1997 | Pinchuk ........................ | 623/12 |

(List continued on next page.)

FOREIGN PATENT DOCUMENTS

| | | |
|---|---|---|
| DE | 44 18 336 A1 | 11/1995 |
| EP | 0740 928 A2 | 11/1996 |
| WO | WO 95/09586 | 4/1995 |
| WO | WO 96/23455 | 8/1996 |
| WO | WO 98/32399 | 7/1998 |

OTHER PUBLICATIONS

"A Self–Expanding Bifurcated Endovascular Graft for Abdominal Aortic Aneurysm Repair", Wilson et al. Slside Forum #3—Access and Vascular Prosthesis.

*Primary Examiner*—Paul B. Prebilic
(74) *Attorney, Agent, or Firm*—Ratner & Prestia

(57) ABSTRACT

Modular endoluminal stent-grafts include at least two different sized stent-grafts which are deployed one within the other. According to one embodiment of the invention, a first stent-graft is provided having a flared end which is expandable to a first diameter and a midsection which is expandable to a second diameter smaller than the first diameter. A second stent-graft is also provided having an end which is expandable to a diameter which engages the midsection of the first stent-graft. The first embodiment of the invention is deployed by expanding the first stent-graft such that its flared end engages a large diameter vessel, then expanding the second stent-graft inside the midsection of the first stent graft and inside a small diameter vessel such that the second stent graft engages the small diameter vessel and the midsection of the first stent-graft. According to a second embodiment of the invention, the midsection of the first stent-graft is reinforced with a flexible member to restrict the midsection from ballooning. According to other aspects of the invention, the first stent-graft is provided with two flared ends and the second stent graft is provided with or without flared ends. According to still another embodiment of the invention, three or more stent-grafts of different expanded diameter are deployed one within the other.

12 Claims, 6 Drawing Sheets

U.S. PATENT DOCUMENTS

| | | | |
|---|---|---|---|
| 5,632,763 A | | 5/1997 | Glastra |
| 5,632,772 A | * | 5/1997 | Alcime et al. ................. 623/1 |
| 5,700,286 A | * | 12/1997 | Tartaglia et al. ............... 623/1 |
| 5,824,040 A | | 10/1998 | Cox et al. |
| 5,861,035 A | * | 1/1999 | Griffith ....................... 623/12 |
| 5,876,448 A | * | 3/1999 | Thompson et al. ........... 623/12 |
| 5,916,264 A | * | 6/1999 | Von Oepen et al. ............ 623/1 |
| 6,110,198 A | * | 8/2000 | Fogarty et al. ............ 623/1.12 |
| 6,203,568 B1 | * | 3/2001 | Lombardi et al. ......... 623/1.13 |

\* cited by examiner

MODULAR ENDOLUMINAL STENT-GRAFTS AND METHODS FOR THEIR USE

This application is a continuation of abandoned Ser. No. 08/806,739 filed Feb. 27, 1997, which is a continuation-in-part of application Ser. No. 08/554,694, entitled "Self-expanding Endoluminal Stent-graft", filed Nov. 7, 1995, now U.S. Pat. No. 5,628,788, the complete disclosures of which are hereby incorporated herein by reference.

BACKGROUND OF THE INVENTION

1. Field of the Invention

The invention relates to an implantable prosthesis. In particular, the invention relates to endoluminal grafts and stent-grafts which are deployed in a blood vessel which has a varying diameter. The invention is particularly suited for repairing the aortic artery and daughter arteries, although it is not limited thereto.

2. State of the Art

An endoluminal stent-graft typically includes tubular graft material which is affixed to the inside or outside of a woven metallic stent and is delivered to the damaged site of a blood vessel via a catheter. Endoluminal stent-grafts are most often used to repair blood vessels affected by a variety of lesions such as stenoses or aneurysms. A typical prior art stent, shown in FIGS. 1–6, is a metallic structure 10 made of braided wire 12 such as stainless steel, cobalt-chromium-nickel super alloys and combinations, co-extrusions or braised combinations of the above with tantalum, gold, platinum and the like. Stents are also made from memory alloys such as nitinol and the like. Typical stents are disclosed in U.S. Pat. Nos. 4,655,771 and 4,954,126 to Wallsten, the complete disclosures of which are hereby incorporated herein by reference, and in U.K. Patent Number 1,205,743 to Didcott, the complete disclosure of which is also hereby incorporated herein by reference. Generally, the wires 12 are braided with a large pick size, i.e. with relatively large interstices 14 between the wires, so that axial expansion of the stent causes a diametrical compression of the stent. Most often the braiding and/or the metal chosen for the wires yields a resilient stent which is self-expanding. However, some stents are not self-expanding and are expanded with the use of a balloon catheter. In the case of self-expanding stents, the proximal and distal ends 16, 18 of the stent are usually flared when expanded.

While endoluminal stents have been used without any graft material when repairing stenoses, it is now generally preferred to use a graft material in combination with the stent when repairing stenoses as well as when repairing aneurysms. The graft material most often used in endoluminal grafts is a PET or polytetrafluroethylene (PTFE) material which is folded to reduce its size and which is attached to one or both ends of a radially expandable stent by means of sutures. When the stent self-expands or is balloon expanded, the graft unfolds around the stent. The above-referenced parent application discloses a stent-graft which incorporates an improved self-expanding graft material.

While the primary use of endoluminal stents is to treat stenoses, stents are also sometimes used in conjunction with graft material to bridge aneurysms. The advantage of using a stent in bridging aneurysms is that the expanded stent helps to fix the graft in place, can eliminate the need for sutures, and may provide some additional resistance to hoop stress. Prior art FIGS. 2–5 illustrate the deployment of a stent-graft to bridge an aneurysm.

Referring now to FIGS. 2–5, the ends of the stent 10 are axially displaced inside an introducer 20 which includes an inner catheter 22 having a soft (dilator) tip 24 and an outer sheath 26. The introducer 20 is delivered through a blood vessel 28 with the aid of a guide wire 30 which is inserted through the lumen of the inner catheter 22. The introducer 20 is guided over the guide wire 30 to the site of an aneurysm, in this case two adjacent aneurysms, namely distal aneurysm 32 and proximal aneurysm 34. With the aid of fluoroscopy, the introducer 20 is positioned so that the soft tip 24 is located distally relative to the distal aneurysm 32. The outer sheath 26 is drawn proximally while the inner catheter 22 is held stationary. This releases the distal end 18 of the stent 10 which self-expands to the inner diameter of the vessel 28 as shown in FIG. 3. Continued proximal movement of the outer sheath 26 releases the remainder of the stent 10 as shown in FIG. 4 until the proximal end 16 of the stent 10 expands to the inner diameter of the vessel 28 proximal of the proximal aneurysm 34 as shown in FIG. 5, after which the introducer 20 and the guide wire 30 are removed from the vessel 28.

From the foregoing, it will be appreciated that by using an appropriately sized stent-graft, the aneurysms 32, 34 in FIGS. 2–5 are effectively bridged utilizing the procedure described above. In particular, the stent-graft must be long enough so that its proximal and distal ends extend beyond the aneurysms and expand into healthy areas of the blood vessel. Moreover, the stent-graft must be chosen to have the appropriate expanded diameter so that a good seal is made between the stent-graft and the inner wall of the blood vessel. However, the diameter should not be so large that when the stent expands, the outward pressure of the expanding stent damages the wall of the blood vessel.

Because of the above considerations, it is difficult or impossible to bridge an aneurysm with a stent-graft when the diameter of the blood vessel on either side of the aneurysm differs by any significant amount. For example, as shown in FIG. 6, the distal end 18 of a stent-graft 10 is greatly compressed as compared to the proximal end 16 when the stent-graft is used to bridge aneurysms 32, 34 where the diameter of the vessel 28 on the proximal side 28a of the aneurysms 32, 34 is substantially greater than the diameter of the vessel on the distal side 28b of the aneurysms 32, 34. Depending on the nature of the particular stent-graft, this can cause damage to the vessel on the distal side 28b or can result in an inward tapering of the distal end 18 of the graft to a "cigar shape". In the former situation, the damage can result in an additional aneurysm or rupture of the vessel. In the latter situation, the distal end 18 of the graft can obstruct the flow of blood, or jeopardize the seal between the distal end 18 and the inner wall of the vessel 28b. In the case of obstruction, occlusion of the vessel may occur which can be catastrophic to the patient. In the case of seal weakening, blood will enter into the aneurysmal sac and promote continued growth of the aneurysm.

More often than not the vessels of the vascular tree especially in the abdominal aortic artery exhibit the joining of vessels having very different diameters. For example, as shown in FIG. 7, the abdominal aortic artery 50 is the trunk from which the renal arteries, right 52, left 54 and the iliac arteries, right 56, left 58 proceed. An aortic aneurysm 60 between the renal arteries and the iliac arteries is very difficult to bridge since the diameter of the aortic artery is approximately 25 mm, whereas the diameter of the iliac artery is about 12 mm. A stent-graft having a diameter of 27 mm will fit well in the aortic artery, but will be too large for the iliac artery. A 13 mm diameter stent-graft will fit well in the iliac artery, but will be too small for the aortic artery.

The above-referenced parent application discloses a bifurcated stent-graft which is useful in repairing an abdominal aortic aneurysm and iliac aneurysm. The bifurcated graft is located in the abdominal aortic artery just above the iliac arteries with its bifurcated end closest to the iliac arteries. The bifurcated stent-graft effectively bypasses an aneurysm in the aortic artery and provides a radiopaque bifurcated guide to the iliac arteries. Once the bifurcated graft is deployed, an additional graft may be deployed in each of the iliac arteries. The additional grafts are deployed through the legs of the bifurcated stent-graft. The bifurcated legs provide separate fluid couplings for the two additional grafts so that blood can flow from the aortic artery to both iliac arteries.

Subsequent to the development of the bifurcated stent-graft of the parent application, additional discoveries have been made regarding the use of multiple stent-grafts to bridge vessels of different diameter. In particular, it is sometimes desirable to bridge the aortic artery with only one of the iliac arteries.

In addition, it has been discovered that in some situations where a stent-graft has been implanted to bridge an aneurysm, the stent-graft will continue to expand radially long after the time of implantation. This is particularly likely where there is continuous progression of aneurysmal disease and dilation of the neck of the aneurysm. The continued radial expansion of the stent-graft results in a continued axial shortening of the stent-graft which often results in the ends of the stent-graft becoming dislodged from the blood vessel whereupon the prosthesis floats free inside the aneurysm causing serious danger to the patient.

SUMMARY OF THE INVENTION

It is therefore an object of the invention to provide endoluminal stent-grafts which are useful for bridging vessels of different diameter.

It is also an object of the invention to provide methods for using endoluminal stent-grafts to bridge vessels of different diameter.

It is still another object of the invention to provide an endoluminal stent-graft with a limited radial expandability and limited axial compressibility.

In accord with these objects which will be discussed in detail below, the modular endoluminal stent-grafts of the present invention include at least two different sized stent-grafts which are deployed one within the other. According to one embodiment of the invention, a first stent-graft is provided having a flared end which is expandable to a first diameter and a midsection which is expandable to a second diameter smaller than the first diameter. A second stent-graft is also provided having an end which is expandable to a diameter which engages the midsection of the first stent-graft. The first embodiment of the invention is deployed by expanding the first stent-graft such that its flared end engages a large diameter vessel, then expanding the second stent-graft inside the midsection of the first stent graft and inside a small diameter vessel such that the second stent graft engages the small diameter vessel and the midsection of the first stent-graft. Both the first and second stent-grafts may be manufactured in a conventional manner using conventional materials. According to a second embodiment of the invention, the midsection of the first stent-graft is reinforced with a flexible member to restrict the midsection from ballooning due to the outward pressure of the second stent-graft deployed within the lumen of the first stent-graft. The reinforcing member may be applied to all or a portion of the stent-graft. The reinforcing member is also useful in preventing the stent-graft from ballooning due to the presence of static blood pressure over time after implantation.

According to other aspects of the invention, the first stent-graft is provided with two flared ends and the second stent graft is provided with or without flared ends.

According to still another embodiment of the invention, three or more stent-grafts of different expanded diameter are deployed one within the other.

According to another embodiment of the invention, two or more stent-grafts of different diameter are pre-coupled to each other prior to deployment and are deployed using a single introducer in substantially one step.

According to still other aspects of the invention, the second and/or third stent-grafts are reinforced with a flexible member to restrict the midsection from ballooning.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
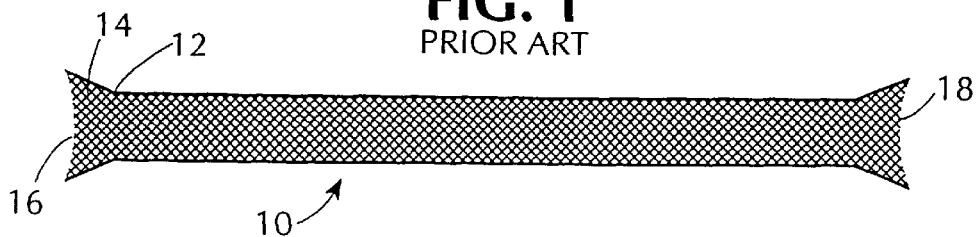
FIG. 1 is a side elevation view of a prior art stent.
Figure 2:
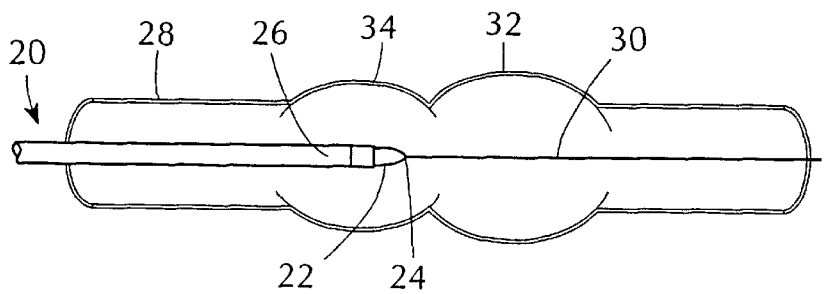
FIG. 2 is a broken side elevation view in partial section of a prior art stent introducer during a first stage of deployment in a blood vessel with two adjacent aneurysms.
Figure 3:
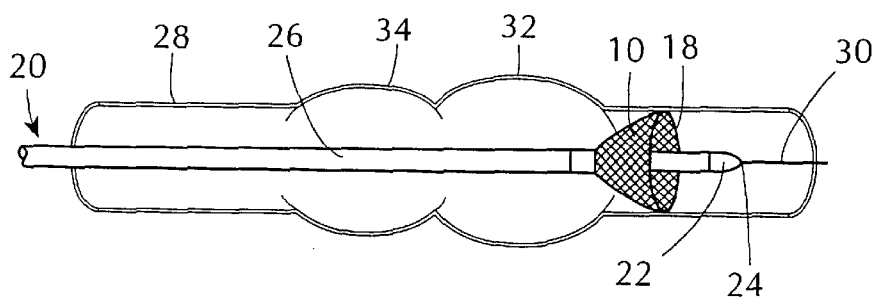
FIGS. 3–5 are views similar to FIG. 2 showing the subsequent stages of deployment according to the prior art.
Figure 4:
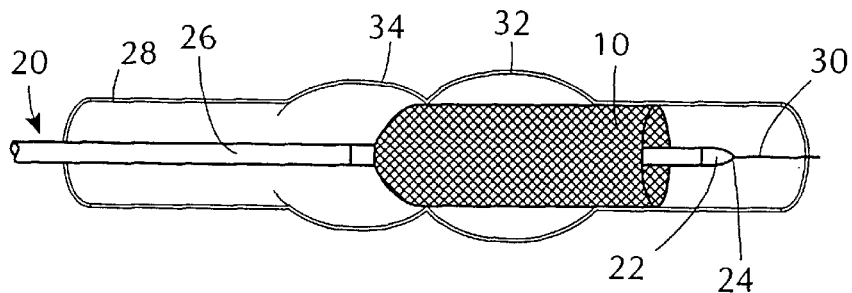
Figure 5:
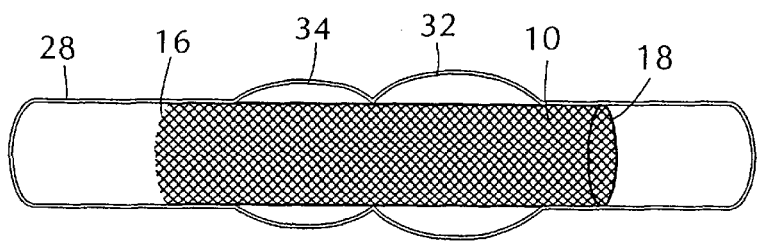
Figure 6:
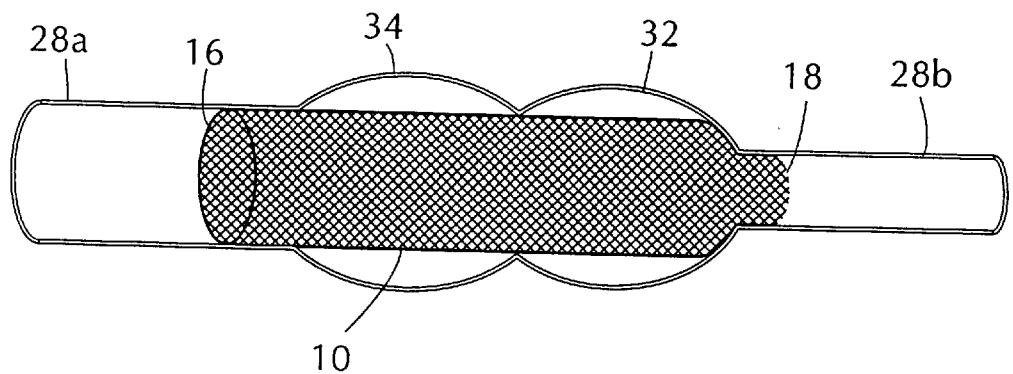
FIG. 6 is a view similar to FIG. 5 showing a blood vessel which has different diameters on either side of the aneurysms.
Figure 7:
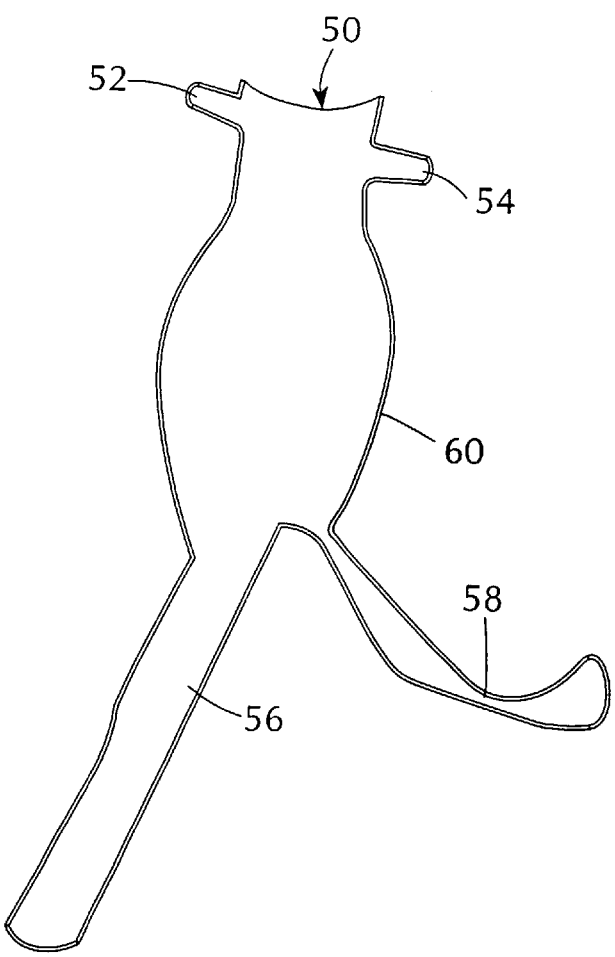
FIG. 7 is a schematic view of an abdominal aortic aneurysm.
Figure 8:
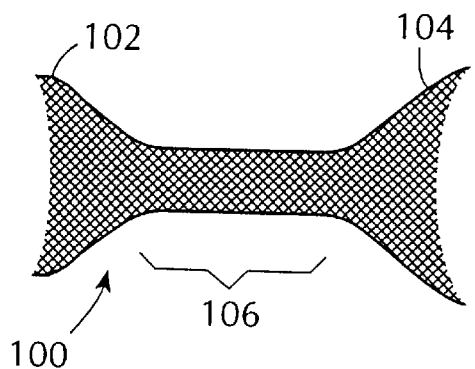
FIG. 8 is a side elevation view of a first stent-graft in a modular system according to the invention.
Figure 9:
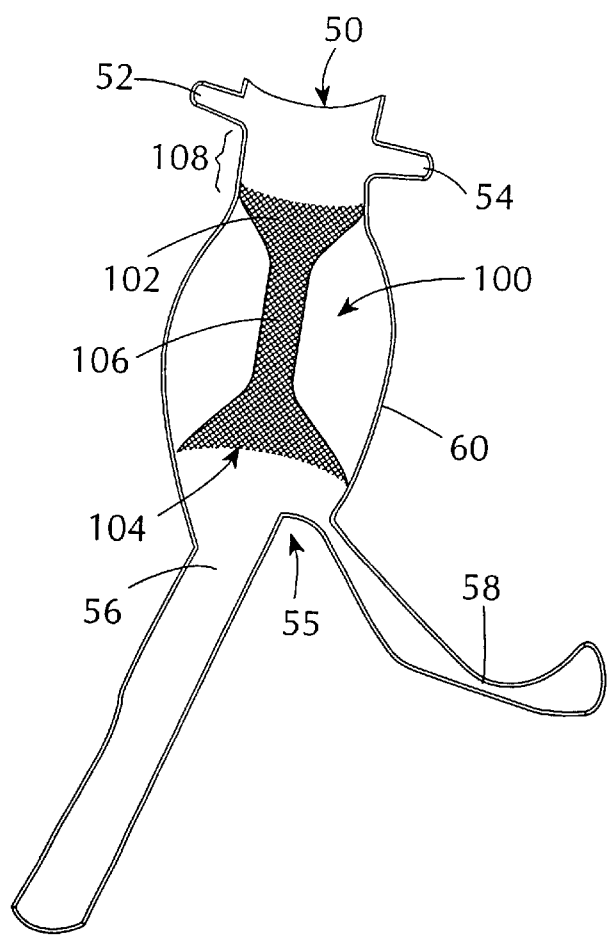
FIG. 9 is a schematic view of the stent-graft of FIG. 8 deployed in an abdominal aortic aneurysm.
Figure 10:
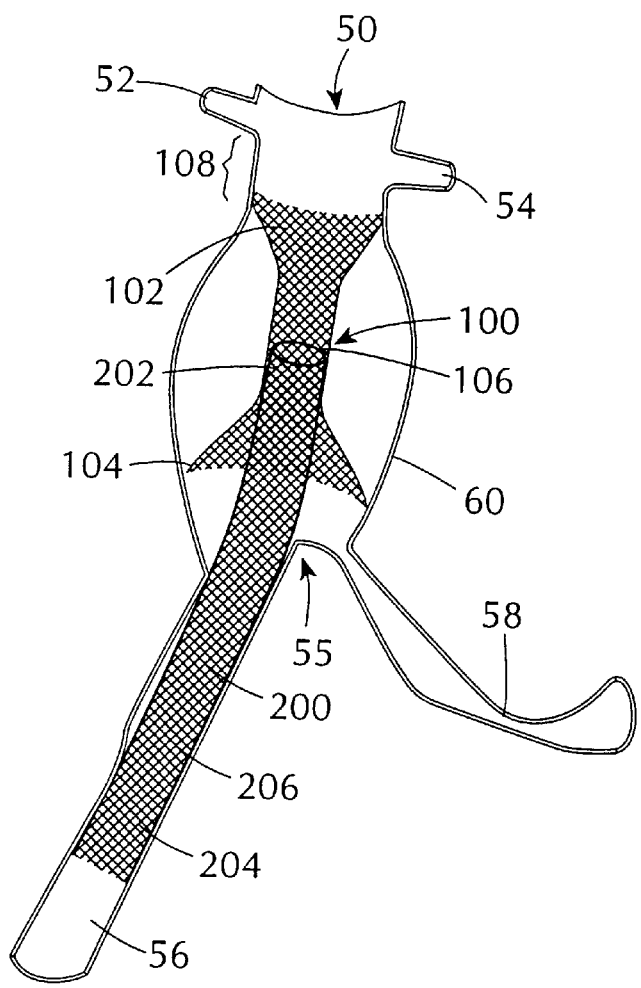
FIG. 10 is a view similar to FIG. 9 showing a second stent-graft in a modular system according to the invention deployed inside the first stent-graft and inside the right iliac artery.

Referring now to FIGS. 8–10, a first stent-graft 100 in a modular system according to the invention has a flared proximal end 102, a flared distal end 104, and a midsection 106. The proximal end 102 is provided with an expanded diameter equal to or slightly larger than the inner diameter of the proximal end of an aneurysm that is to be bridged, e.g. the neck 108 of the abdominal aortic artery 50. The midsection 106 is provided with an expanded diameter equal to or slightly smaller than the inner diameter of the distal end 55 of an aneurysm that is to be bridged, e.g. the right iliac artery 56. The stent-graft 100 may be manufactured according to conventional methods with conventional materials, but is preferably manufactured using the methods and materials described in the above-referenced parent application. A second stent-graft 200 in a modular system according to the invention has a proximal end 202, a distal end 204, and a midsection 206. The expanded diameter of the proximal end 202 is dimensioned to engage the expanded interior of the midsection 106 of the first stent-graft 100 and the expanded diameter of the distal end 204 is dimensioned to engage the interior of the distal end of an aneurysm that is to be bridged, e.g. the right iliac artery 56. The stent-graft 200 may be manufactured according to conventional methods with conventional materials, but is preferably manufactured using the methods and materials described in the above-referenced parent application.

The modular stent-grafts 100 and 200 are deployed in the following manner which is illustrated by way of example in FIGS. 9 and 10 which depict deployment in an abdominal aortic aneurysm. The first stent-graft 100 is compressed into an introducer (not shown) and delivered to the a point distal of the renal arteries 52, 54 using conventional methods (see FIGS. 2–5). The stent-graft 100 is deployed such that the proximal end 102 of the stent-graft 100 expands into the neck 108 of the aortic artery distal of the renal arteries 52, 54 but proximal of the aortic aneurysm 60. The expanded distal end 104 rests in the aneurysm itself and serves to stabilize the position of the midsection 106 as shown in FIG. 9. The introducer (not shown) is withdrawn and the second stent-graft 200 is compressed into the same or another introducer and delivered through the first stent-graft 100 to a point within the right iliac artery 56. The second stent-graft 200 is deployed such that the proximal end 202 of the second stent-graft expands into the midsection 106 of the first stent-graft 100 and the distal end 204 of the second stent-graft expands into the right iliac artery.

As mentioned above, both the first and second stent-grafts may be manufactured according to conventional methods with conventional materials or using the methods and materials described in the above-referenced parent application. In addition, the second stent-graft may be made with fewer wires and/or with smaller wires in order that it fit properly in the iliac artery. The first stent-graft 100 may also be provided with midsection reinforcement as shown in FIG. 11.

Figure 11:
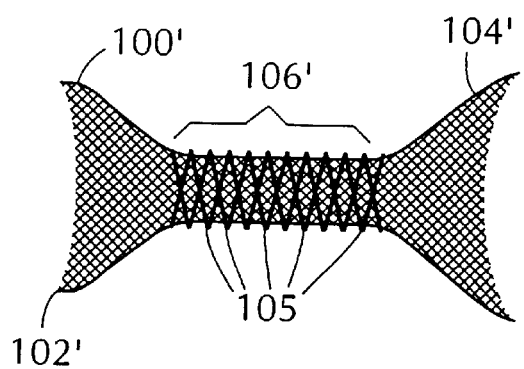
FIG. 11 is a side elevation view of a second embodiment of a first stent-graft according to the invention having a flexible reinforcement.

Turning now to FIG. 11, there is illustrated a stent-graft 100' which is similar to the first stent-graft 100 described above. The stent-graft 100' has a flared proximal end 102', a flared distal end 104', and a midsection 106'. According to this embodiment, the stent-graft 100' has a flexible reinforcement 105' attached to the midsection 106' which restricts the midsection from ballooning when another (second) stent-graft is expanded inside the midsection. The flexible reinforcement 105' may be formed from sutures, knits, weaves, braids, wires, or another stent. The reinforcement 105' may be attached to the inside or the outside of the midsection. Suitable materials for the reinforcement 105' include polyethylene terphthalate, nylon, polytetrafluoroethylene, polyolefin, polyamide, polycarbonate, polycarbonate urethane, metallic wire such as tantalum, stainless steel, titanium, annealed cobalt-chromium-nickel, etc. The reinforcement may be attached to the stent by suturing, gluing, hooks, welds or any other method which does not interfere with the compression of the stent. As shown in FIG. 11, the reinforcement 105' is a substantially continuous member or members. In addition, such a reinforcement may be applied to all or part of the second stent-graft 200 described above in order to prevent ballooning of the second stent-graft in regions of high blood pressure, or in instances where the stent-graft is compressed axially during deployment.

Figure 11B:
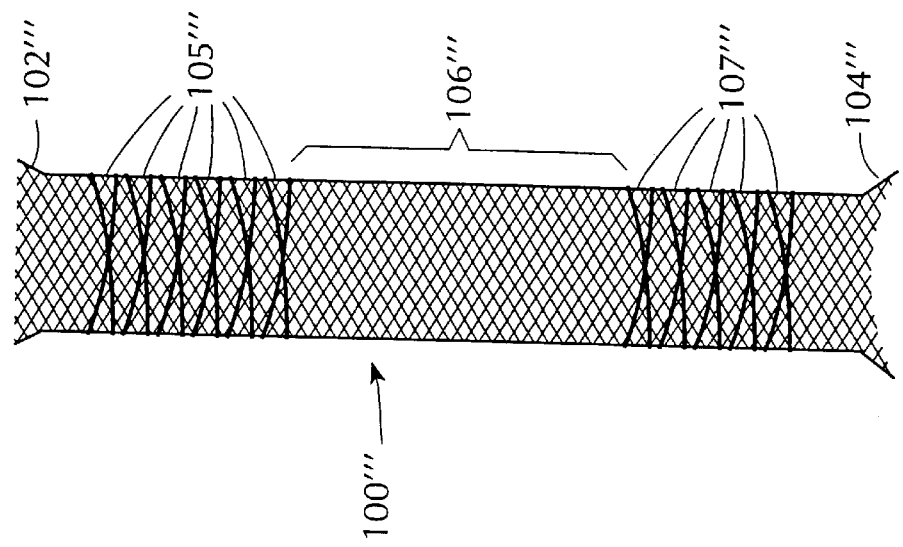
FIG. 11b is a view similar to FIG. 11a of a stent-graft according to the invention having still another type of flexible reinforcement.
Figure 11A:
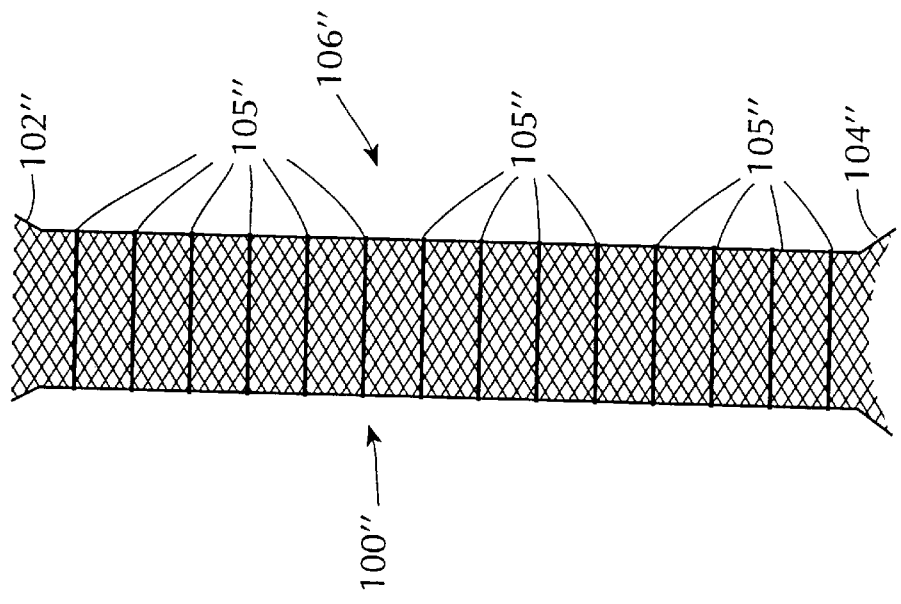
FIG. 11a is a view similar to FIG. 11 of a stent-graft according to the invention having another type of flexible reinforcement.

Turning now to FIG. 11a, there is shown a stent-graft 100" which is similar to the first stent-graft 100 described above. The stent-graft 100" has a flared proximal end 102", a flared distal end 104", and a midsection 106". According to this embodiment, the stent-graft 100" has a flexible reinforcement 105" attached to the midsection 106" and extending along substantially its entire length. In addition, in this embodiment, the reinforcement is formed from a series of discrete members which are axially spaced apart from each other. An advantage of using discrete members is that the stent-graft can be trimmed on the operating table without risking detachment of the ends of the reinforcement. This advantage can also be achieved with a reinforcement which is inlay knitted or woven into the graft component of the stent-graft, a reinforcement which is added to the outside of the stent-graft, or a reinforcement which is located between the stent and the graft.

FIG. 11b shows a stent-graft 100''' which is similar to the first stent-graft 100 described above. The stent-graft 100''' has a flared proximal end 102''', a flared distal end 104''', and a midsection 106'''. According to this embodiment, the stent-graft 100''' has a first flexible reinforcement 105''' located between the proximal end 102''' and the midsection 106''' and a second flexible reinforcement 107''' located between the distal end 104''' and the midsection 106'''. An advantage of this configuration is that it allows a small amount of additional axial compressibility which can be helpful during deployment. For example, if the stent is too long, it can be compressed axially to fit in the desired space. In addition, the pitch angle of the reinforcements 105''', 107''' can be made lower to add a small amount of longitudinal compressibility to the stent-graft while still maintaining a restriction on the radial expandability of the stent-graft.

Common to all of the embodiments of the reinforced stent-graft is the feature that the reinforcement is flexible enough to allow the stent-graft to be pulled down to a small diameter for delivery to the deployment site, but be strong enough to limit the radial expansion of the stent-graft beyond a diameter which is substantially equal to the resting diameter of the stent-graft.

Figure 12:
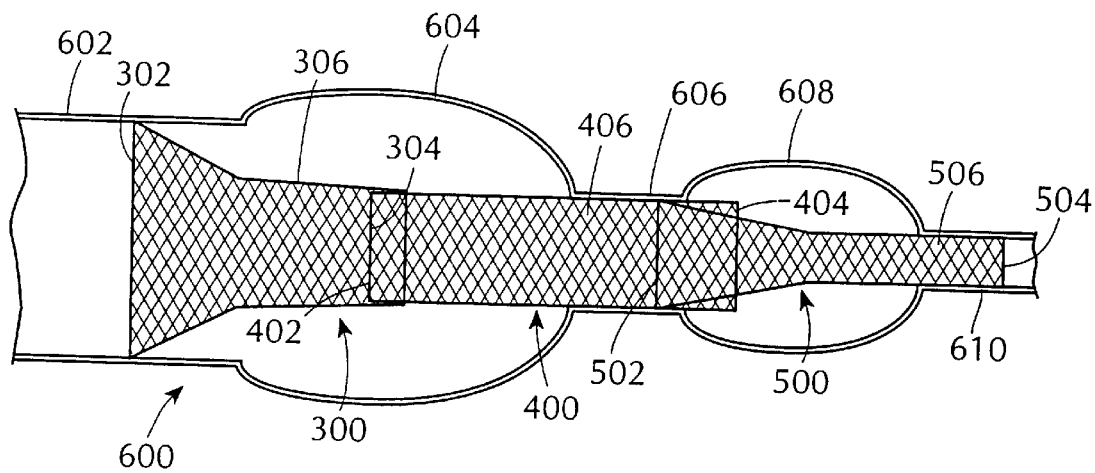
FIG. 12 is a schematic view of a modular stent-graft system according to the invention having three stent-grafts where the second is deployed inside the first and the third is deployed inside the second.

The modular stent-graft system of the invention may include more than two stent-grafts. For example, as shown in FIG. 12, a modular system may include three stent-grafts 300, 400, 500 for bridging two aneurysms 604, 608 in a blood vessel 600 which exhibits three different diameters 602, 606, 610. As shown in FIG. 12, the first stent-graft 300 has a flared proximal end 302, a non-flared distal end 304, and a midsection 306. The second stent-graft 400 has a non-flared proximal end 402, a non-flared distal end 404, and a midsection 406. The third stent-graft 500 has a flared proximal end 502, a non-flared distal end 504, and a midsection 506. The flared proximal end 302 of the first stent-graft 300 has an expanded diameter which fits securely in the large diameter portion 602 of the blood vessel 600 proximal of the first aneurysm 604. The second stent-graft 400 has a substantially constant expanded diameter which causes its proximal end 402 to fit securely in the midsection 306 of the first stent-graft 300 and its midsection 406 to fit securely in the smaller diameter section 606 of the blood vessel 600 between the first aneurysm 604 and the second aneurysm 608. The flared proximal end 502 of the third stent-graft 500 has an expanded diameter which fits securely in the midsection 406 of the second stent-graft 400; and the non-flared distal end 504 has an expanded diameter which fits securely in the smallest diameter portion 610 of the blood vessel 600 distal of the second aneurysm 608. The modular stent-grafts of FIG. 12 are deployed in a manner similar to the stent-grafts shown in FIG. 10, i.e. by deploying the proximal stent-graft first, and then following with distal stent-grafts. Although FIG. 12 shows three stent-grafts with increasingly smaller diameters, the proximal to distal diameter change need not be from larger to smaller. For example, if the aneurysm 608 were located proximal of the aneurysm 604, the stent-grafts could be deployed in a different order or in the same order but with their proximal and distal ends reversed. That is, the stent-graft 400 could be deployed first and the stent-grafts 300 and 500 could be deployed inside the stent-graft 400. In this situation, it would be advantageous for the entire length of the stent-graft 400 to be reinforced. Alternatively, the stent-graft 300 could be deployed first with its end 302 being deployed distally, etc.

Figure 13:
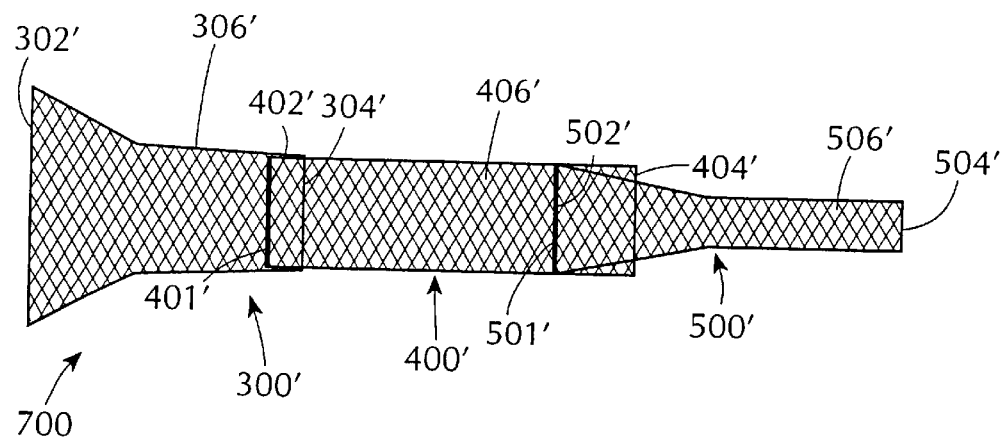
FIG. 13 is a schematic view of a modular stent-graft system according to the invention in which stent-grafts of different diameter are pre-coupled to each other prior to deployment.
Figure 14:
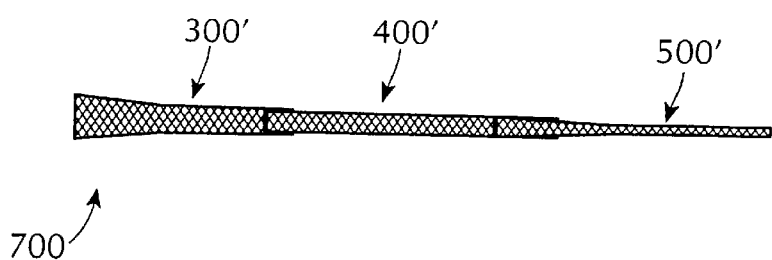
FIG. 14 is a reduced schematic view of the stent-graft system of FIG. 13 in a "pulled-down" state.

Referring now to FIGS. 13 and 14, a modular stent-graft system 700 is shown. The stent-graft system 700 has three stent-grafts 300', 400', and 500' which are similar to the stent-grafts 300, 400, and 500 described above. As shown in FIG. 13, the primed reference numerals (e.g. 302') refer to features of the stent-grafts 300', 400', and 500' which are similar to features of the stent-grafts 300, 400, and 500 described above. According to this embodiment of the invention, the proximal end 402' of the stent-graft 400' is pre-coupled to the midsection 306' of the stent-graft 300' and the proximal end 502' of the stent-graft 500' is pre-coupled to the midsection 406' of the stent-graft 400'. The pre-coupling may be effected at the time of manufacture, or by a practitioner prior to deployment of the modular stent-graft system. As shown in FIG. 13, the pre-coupling is accomplished with sutures 401' and 501'. However, the stent-grafts may also be coupled to each other by wires, adhesives, welds, or by using any other suitable coupling method. After the stent-grafts 300', 400', and 500' are coupled to each other, they are "pulled down" as a single unit with the aid of an introducer to a compressed state as shown in FIG. 14 for deployment.

There have been described and illustrated herein several embodiments of modular endoluminal stent-grafts and methods for their use. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while the stent-grafts have been shown for use in bridging aneurysms, it will be recognized that the modular system of stent-grafts could be used to bridge other types of lesions. Moreover, while particular configurations have been disclosed in reference to flared ends and reinforcing members, it will be appreciated that other configurations could be used as well. For example, the modular stent-graft 100 described with reference to FIG. 10 could be provided with a single flared end, the proximal end, rather than two flared ends, in order to fit in certain tortuous arteries. Also, it is possible to utilize a bifurcated stent (as shown in the parent application) as a component in a modular stent system and use an occluding device to block one of its legs.

It will therefore be appreciated by those skilled in the art that yet other modifications could be made to the provided invention without deviating from its spirit and scope as so claimed.

What is claimed is:

1. A modular endoluminal stent-graft system for bridging a lesion in a blood vessel, said blood vessel having a large diameter on a proximal side of the lesion, a small diameter on the distal side of the lesion, and an intermediate region between said proximal side and said distal side, said intermediate region having a diameter larger than said large diameter, said system comprising a first stent-graft and a second stent-graft, both stent-grafts having a contracted state for insertion into the vessel and an expanded state upon deployment in the vessel;

wherein:
   a) the first stent-graft has a flared proximal end, a flared distal end, and a midsection, said flared proximal end having an expanded diameter at its tip adapted to be equal to or slightly larger than the large diameter of the blood vessel; and
   b) the second stent-graft has a proximal end and a distal end, said proximal end having an expanded diameter equal to or slightly larger than said expanded diameter of said midsection of said first stent graft, and said distal end having an expanded diameter which is adapted to be equal to or slightly larger than the small diameter of the blood vessel;

and wherein:
   said flared distal end of said first stent-graft is adapted to directly engage the wall of the blood vessel in said intermediate region; and
   said distal end of said second stent graft is adapted to engage the small diameter of the blood vessel.

2. The modular stent-graft system of claim 1, wherein said proximal end of said second stent-graft is adapted to securely engage said midsection of said first stent-graft to hold said second stent-graft substantially fixed relative to said first stent-graft.

3. The modular stent-graft system of claim 1, wherein said proximal end of said second stent-graft is coupled to said first stent-graft such that a common lumen is thus defined.

4. A system according to claim 1, wherein:
said proximal end of said second stent-graft is flared.

5. A system according to claim 1, wherein:
said distal end of said second stent-graft is flared.

6. A system according to claim 1, wherein:
at least said midsection of said first stent-graft is reinforced with a flexible material.

7. A system according to claim 6, wherein:
said flexible material is selected from the group consisting of polyethylene terphthalate, nylon, polytetrafluoroethylene, polyolefin, polyamide, polycarbonate, polycarbonate urethane, and metallic wire.

8. A system according to claim 6, wherein:
said flexible material is selected from the group consisting of sutures, knits, weaves, braids, wires, and stents.

9. A system according to claim 1, further comprising:
   c) a third stent-graft having a first end, a second, end, and a midsection, said first end of said third stent-graft having an expanded fifth diameter, wherein said midsection of said second stent-graft has an expanded sixth diameter equal to or slightly smaller than said expanded fifth diameter of said first end of said third stent-graft, such that in a deployed orientation, said first end of said third stent-graft engages said midsection of said second stent-graft.

10. A system according to claim 9, wherein:

said proximal end of said third stent-graft is flared.

11. A system according to claim 1, wherein:

said proximal end of said second stent-graft is coupled to said first stent-graft by a coupling material selected from the group consisting of sutures, wires, adhesive and welds.

12. A system according to claim 1, wherein:

said proximal end of said second stent-graft is coupled to said midsection of said first stent-graft.

* * * * *